United States Patent
Okamoto et al.

(10) Patent No.: US 6,267,981 B1
(45) Date of Patent: Jul. 31, 2001

(54) METHOD OF PRODUCING SUSTAINED-RELEASE PREPARATION

(75) Inventors: Kayoko Okamoto, Osaka; Yutaka Yamagata, Hyogo; Yasutaka Igari, Hyogo; Masafumi Misaki, Hyogo, all of (JP)

(73) Assignee: Takeda Chemical Industries, Ltd., Osaka (JP)

( * ) Notice: Subject to any disclaimer, the term of this patent is extended or adjusted under 35 U.S.C. 154(b) by 0 days.

(21) Appl. No.: 09/571,728

(22) Filed: May 15, 2000

Related U.S. Application Data

(63) Continuation of application No. 08/714,044, filed as application No. PCT/JP96/01770 on Jun. 26, 1996, now abandoned.

(30) Foreign Application Priority Data

Jun. 27, 1995 (JP) .................................................. 7-161204
Apr. 24, 1996 (JP) .................................................. 8-102403

(51) Int. Cl.[7] ................ A61F 2/00; A61K 9/50; A61K 9/14; A61K 38/28; C07K 14/00
(52) U.S. Cl. .............. 424/426; 424/422; 424/489; 424/499; 514/2; 514/3; 530/350; 530/389.2; 530/388.24; 530/399
(58) Field of Search ............... 424/499, 489, 424/422, 426; 514/2, 3; 530/350, 399, 388.24, 389.2

(56) References Cited

U.S. PATENT DOCUMENTS

| | | |
|---|---|---|
| 4,568,536 | 2/1986 | Kronenthal et al. ............ 424/22 |
| 4,650,665 | 3/1987 | Kronenthal et al. ............ 424/435 |
| 5,192,741 | 3/1993 | Orsolini et al. . |
| 5,271,945 | 12/1993 | Yoshioka et al. . |
| 5,445,832 | 8/1995 | Orsolini et al. . |
| 5,480,656 | 1/1996 | Okada et al. . |
| 5,503,851 | 4/1996 | Mank et al. ............ 424/489 |
| 5,534,269 | 7/1996 | Igari et al. . |
| 5,643,607 | 7/1997 | Okada et al. . |
| 6,087,324 | * 7/2000 | Igari et al. . |

FOREIGN PATENT DOCUMENTS

| | | |
|---|---|---|
| 0 216 485 | 4/1987 | (EP) . |
| 0461630 | 12/1991 | (EP) . |
| 0 467 389 | 1/1992 | (EP) . |
| 0579347 | 1/1994 | (EP) . |
| 0 633 020 | 1/1995 | (EP) . |
| 0633020 | 1/1995 | (EP) . |
| 93/17668 | 9/1993 | (WO) . |
| 94/12158 | 6/1994 | (WO) . |
| 29664 | 11/1995 | (WO) . |

OTHER PUBLICATIONS

Wada et al., J. Pharm. Pharmacol., No. 43 (1991) 605–608.

* cited by examiner

Primary Examiner—Thurman K. Page
Assistant Examiner—Brian K. Seidleck
(74) Attorney, Agent, or Firm—Fitzpatrick, Cella, Harper & Scinto

(57) ABSTRACT

This invention provides a sustained-release preparation comprising a biodegradable polymer metal salt and broactive polypeptide, with enhanced entrapment of the bioactive polypeptides, a suppression of initial burst, and a constant long-term release of the bioactive polypeptides.

21 Claims, No Drawings

METHOD OF PRODUCING SUSTAINED-RELEASE PREPARATION

This application is a continuation of application Ser. No. 08/714,044 filed Sep. 5, 1996, now abandoned which is a 371 of PCT/JP96/01770, filed Jun. 26, 1996.

TECHNICAL FIELD

The present invention relates to a sustained-release preparation comprising a biodegradable polymer metal salt and a bioactive polypeptide, and a method of producing thereof.

BACKGROUND ART

It is known that bioactive polypeptides or their derivatives exhibit a variety of pharmacologic activities in vivo. Some of these polypeptides have been produced on a large scale by utilizing *Escherichia coli,* yeasts, animal cells or host animals such as hamsters using recently developed genetic engineering and cell technology, and put to medicinal use. However, these bioactive polypeptides must be frequently administered because of the generally short biological half-life. The repeated injections takes a significant physical burden on patients. To overcome this disadvantage, various attempts have been made to develop sustained-release preparations comprising bioactive polypeptides.

EP-461630 discloses prior art production technologies for sustained-release preparations designed for the enhanced efficiency of entrapment of water-soluble bioactive peptides. These preparations are obtained from an oil/water (o/w) emulsion comprising dissolving a water-soluble bioactive polypeptide, a biodegradable polymer and a fatty acid salt in an organic solvent.

Although various attempts have been made to produce a sustained-release preparation retaining the bioactivity of bioactive polypeptides as mentioned above, there has not been a clinically satisfactory sustained-release preparation with efficiencient entrapment of a bioactive polypeptide into a biodegradable polymer, and suppression of initial drug burst, constant long-term drug release, and so on.

DISCLOSURE OF INVENTION

The present inventors made extensives investigations to resolve the above problems, and found that sustained-release preparations dispersing a bioactive polypeptide in an organic solvent containing a biodegradable polymer pre-converted to a metal salt, and subjecting the resulting dispersion to formulation have unexpected excellent properties such as a surprising enhancement of entrapment of bioactive polypeptides, suppression of initial burst of the polypeptides, constant long-term release, and so on. The present invention has been developed after further elaborations based on the above findings.

The present invention, therefore, is directed to:

(1) a method of producing a sustained-release preparation which comprises dispersing a bioactive polypeptide in an organic solvent containing a biodegradable polymer metal salt, and subjecting the resulting dispersion to formation, (2) a method according to (1), wherein the metal salt is a polyvalent metal salt, (3) a method according to (1), wherein the metal salt is selected from the group consisting of a zinc salt and a calcium salt, (4) a method according to (1), wherein the organic solvent is a mixture of halogenated hydrocarbons and acetonitrile or alcohols, (5) a method according to (4), wherein the organic solvent mixture ratio of haloganated hydrocarbons to acetonitrile or alcohols is in the range of about 40:1 to about 1:1 (volume/volume), (6) a method according to (1), wherein the bioactive polypeptide is a hormone, (7) a method according to (6), wherein the hormone is an insulin, (8) a method according to (6), wherein the hormone is a growth hormone, (9) a method according to (1), wherein the bioactive polypeptide is a cytokine,

(10) a method according to (9), wherein the cytokine is an interferon,

(11) a method according to (1), wherein the biodegradable polymer is an aliphatic polyester,

(12) a method according to (11), wherein the aliphatic polyester is an α-hydroxycarboxylic acid polymer,

(13) a method according to (11), wherein the aliphatic polyester is a lactic acid-glycolic acid copolymer,

(14) a method according to (13), wherein the composition ratio (mol %) of lactic acid/glycolic acid of the lactic acid-glycolic acid copolymer is about 100/0 to about 40/60, and the weight-average molecular weight of the lactic acid-glycolic acid copolymer is about 3,000 to about 20,000,

(15) a method according to (1), wherein the sustained-release preparation is a particulate artifact,

(16) a method according to (15), wherein the average particle size of the particulate artifact is about 0.1 μm to about 300 μm,

(17) a method according to (1), wherein the sustained-release preparation is for an injection,

(18) a dispersion which comprises a bioactive polypeptide dispersed in an organic solvent containing a biodegradable polymer metal salt,

(19) a sustained-release preparation as produced by the method according to (1),

(20) a sustained-release preparation according to (19), wherein the metal content of the biodegradable polymer metal salt is about 0.01 to about 10% by weight,

(21) a sustained-release preparation according to (19), wherein the concentration of the bioactive polypeptide is about 0.001 to about 30% (w/w), and

(22) a sustained-release preparation according to (19), wherein the bioactive polypeptide is a growth hormone, and so on.

The biodegradable polymer of the present invention has low water soluability or is water-insoluble, and includes aliphatic polyesters, e.g., homopolymers or copolymers synthesized from one or more kinds of α-hydroxycarboxylic acids (e.g., glycolic acid, lactic acid, 2-hydroxybutyric acid, valinic acid, leucic acid, etc.), hydroxydicarboxylic acids (e.g., malic acid, etc.), hydroxytricarboxylic acids (e.g., citric acid, etc.), or their mixtures; poly-α-cyanoacrylic esters, e.g., poly(methyl α-cyanoacrylate), poly(ethyl α-cyanoacrylate), poly(butyl α-cyanoacrylate), etc.; and amino acid polymers, e.g., poly(γ-benzyl-L-glutamate) etc., or their mixtures. The mode of polymerization for these biodegradable polymer may be any of random, block or graft polymerizations technique.

The preferred biodegradable polymers are aliphatic polyesters, e.g., homopolymers or copolymers synthesized from one or more kinds of α-hydroxycarboxylic acids (e.g., glycolic acid, lactic acid, 2-hydroxybutyric acid, etc.), hydroxydicarboxylic acids (e.g., malic acid, etc.) and hydroxytricarboxylic acids (e.g., citric acid, etc.), or their mixtures, and so on.

Among the above-mentioned aliphatic polyesters, the homopolymers and copolymers synthesized from one or more kinds of the α-hydroxycarboxylic acids are preferable in view of biodegradability and biocompatibility. Particularly preferred aliphatic polyesters are copolymers synthesized from two or more kinds of the α-hydroxycarboxylic acids. Furthermore, these copolymers can be used as mixtures.

When the α-hydroxycarboxylic acids are chiral compounds, they may be any of D-, L- and D-, L-configuration. It is preferable that the ratio of the D-/L-configuration (mol %) is in the range of about 75/25 to about 25/75. More preferred is a hydroxycarboxylic acid wherein the ratio of the D-/L-configuration (mol %) is in the range of about 60/40 to about 30/70.

An examples of the above mentioned α-hydroxycarboxylic acid polymer is a lactic acid polymer (hereinafter sometimes referred to as "polylactic acid").

The α-hydroxycarboxylic acid copolymer includes copolymers of glycolic acid with the other α-hydroxycarboxylic acids such as lactic acid and 2-hydroxybutyric acid.

Preferred α-hydroxycarboxylic acid copolymers are lactic acid-glycolic acid copolymer and 2-hydroxybutyric acid-glycolic acid copolymer.

A particularly preferred α-hydroxycarboxylic acid copolymer is a lactic acid-glycolic acid copolymer.

The polylactic acid may be either D-configuration or L-configuration or a mixture; one with the D-/L-configuration ratio (mol %) of about 75/25 to about 20/80 is preferred. More preferred is a polylactic acid wherein the ratio of the D-/L-configuration (mol %) is in the range of about 60/40 to about 25/75. Most preferred is a polylactic acid wherein the ratio of D-/L-configuration is in the range of about 55/45 to about 25/75.

The polylactic acid preferably has the weight average molecular weight, as defined below, of about 1,500 to about 10,000. More preferred is a polylactic acid having the weight average molecular weight of about 2,000 to about 8,000. Particularly preferred is a polylactic acid having the weight average molecular weight of about 3,000 to about 6,000. The dispersity (weight average molecular weight/number average molecular weight) of polylactic acid is preferably in the range of about 1.2 to about 4.0, and more preferably in the range of about 1.5 to about 3.5.

The polylactic acid can be produced by the prior art methods described in EP-172636 (e.g., by dehydrative polycondensation in the absence of a catalyst or by dehydrative polycondensation in the presence of an inorganic solid acid catalyst). The preferred polylactic acid is produced by dehydrative polycondensation in the absence of a catalyst.

The compositional ratio (lactic acid/glycolic acid, mol %) in the lactic acid-glycolic acid copolymer is preferably about 100/0 to about 40/60, more preferably about 90/10 to about 45/55, and most preferably about 60/40 to about 40/60. The weight average molecular weight of the lactic acid-glycolic acid copolymer is preferably about 3,000 to about 20,000, and more preferably about 4,000 to about 15,000. The dispersity (weight average molecular weight/number average molecular weight) of the lactic acid-glycolic acid copolymer is preferably about 1.2 to about 4.0, and more preferably about 1.5 to about 3.5.

The lactic acid-glycolic acid copolymers can be produced by the known methods described in EP-172636 (e.g., dehydrative polycondensation in the absence of a catalyst or dehydrative polycondensation in the presence of an inorganic solid acid catalyst). The preferred copolymer is one produced by dehydrative polycondensation in the absence of a catalyst.

In the present invention, two kinds of lactic acid-glycolic acid copolymers differing in compositional ratio and weight average molecular weight can be used in an admixture of any ratio. The typical example is a mixture of a lactic acid-glycolic acid copolymer wherein the compositional ratio of the lactic acid/glycolic acid (mol %) is about 75/25 and the weight average molecular weight is about 6,000. Another example is lactic acid-glycolic acid copolymer wherein the compositional ratio of the lactic acid/glycolic acid (mol %) is about 50/50 and the weight average molecular weight is about 4,000. The preferred weight ratio of the mixture is about 25/75 to about 75/25.

The compositional ratio of the 2-hydroxybutyric acid-glycolic acid copolymer is about 10 to about 75 mol % of glycolic acid and the remaining mol % of 2-hydroxybutyric acid, more preferably about 20 to about 75 mol % of glycolic acid, and more preferably about 30 to about 70 mol % of glycolic acid. The weight average molecular weight of 2-hydroxybutyric acid-glycolic acid copolymer is preferably about 2,000 to about 30,000, and more preferably about 3,000 to about 20,000. The particularly preferred weight average molecular weight of the copolymer is about 4,000 to about 15,000. The dispersity (weight average molecular weight/number average molecular weight) of 2-hydroxybutyric acid-glycolic acid copolymer is preferably about 1.2 to about 4.0, and more preferably about 1.5 to about 3.5.

2-Hydroxybutyric acid-glycolic acid copolymers can be produced by the known methods described in EP-172636 (e.g., dehydrative polycondensation in the absence of a catalyst or dehydrative polycondensation in the presence of an inorganic solid acid catalyst). The preferred copolymer is one produced by dehydrative polycondensation in the absence of a catalyst.

The glycolic acid copolymers (e.g., lactic acid-glycolic acid copolymer, 2-hydroxybutyric acid-glycolic acid copolymer, etc.) may be used in an admixture with polylactic acid. When glycolic acid copolymer is used in combination with polylactic acid, the ratio of glycolic acid copolymer/polylactic acid (weight %) may be, for example, about 10/90 to about 90/10. The preferred ratio is about 20/80 to about 80/20, and the most preferred ratio is about 30/70 to about 70/30.

The terms "weight average molecular weight" and "number average molecular weight" as used in this specification mean the polystyrene equivalent average molecular weight and number average molecular weight of a sample as determined by gel permeation chromatography (GPC) using 9 polystyrene standards having the weight average molecular weights of 120,000, 52,000, 22,000, 9,200, 5,050, 2,950, 1,050, 580 and 162. These determinations can be made using GPC Column KF804L×2 (Showa Denko K. K.), RI Monitor L-3300 (Hitachi, Ltd.), and chloroform as the mobile phase.

In the present invention, biodegradable polymers synthesized by the dehydrative polycondensation reaction in the absence of a catalyst have free carboxyl groups at the terminus.

Such biodegradable polymers having free carboxyl groups at the terminus feature a high correlation between the number average molecular weight determined by end-group titrimetric assay and the number average molecular weight determined by GPC assay using polystyrene standards of known molecular weights, as previously described.

By the end-group assay method, the number average molecular weight can be determined in the following manner.

About 1 g to 3 g of the biodegradable polymer is dissolved in a mixed solvent of acetone (25 ml) and methanol (5 ml), and the carboxyl groups in the solution are quickly titrated with 0.05N alcoholic potassium hydroxide solution using phenolphthalein as indicator under stirring at room temperature (about 0 to about 30° C.). The number average molecular weight is calculated by the following equation.

Number average molecular weight by end-group assay=20000 (A/B)

A: the weight mass (g) of biodegradable polymer
B: the amount (ml) of 0.05N alcoholic KOH solution added until end-point is reached In the case of a biodegradable polymer having free carboxyl groups at the terminal which is synthesized from one or more kinds of α-hydroxy acids by dehydrative polycondensation in the absence of a catalyst, a high correlation is found between the number average molecular weight determined by GPC assay and the number average molecular weight determined by the end-group assay. In contrast, in the case of a biodegradable polymer produced from the cyclic dimer of an α-hydroxy acid by the ring-opening polymerization method using a catalyst and having essentially no free carboxyl groups at the terminus, the number average molecular weight found by the end-group assay is considerably higher than the number average molecular weight found by GPC. Because of this difference, a biodegradable polymer having free carboxyl groups at the terminal can easily be differentiated from a biodegradable polymer not having free carboxyl groups at the terminus.

Whereas the number average molecular weight found by the end-group assay is an absolute value, the number average molecular weight found by GPC assay is a relative value dependent on many variables such as analytical methods and conditions (e.g., the types of mobile phase and column, reference standard, choice of slicing width, selection of baseline, etc.) and, therefore, is hard to generalize. However, a high correlation exists between the number average molecular weight found by end-group assay and the number average molecular weight found by the GPC assay when the value obtained from the end-group assay is within the range of about 0.5 to about 2.0 times the value found by the GPC assay. The preferred range is about 0.8 to about 1.5 times. That the number average molecular weight found by end-group assay is "considerably higher" than the number average molecular weight found by GPC means that the value found by the end-group assay is more than about twice the value found by the GPC assay.

In the present invention, the preferred polymers are those showing a high correlation between the number average molecular weight found by the end-group assay and the number average molecular weight found by the GPC assay.

The metal salts which can be used for converting a biodegradable polymer to its metal salt is not particularly limited as far as it does not exert bad influences in vivo. The metal salt includes a salt formed by a monovalent metal such as alkali metals (e.g., sodium, potassium, etc.) or alkaline earth metals (e.g., calcium, magnesium, etc.), or a polyvalent metal such as zinc (II), iron (II, III), copper (II), tin (II, IV), and aluminum (II, III) with an inorganic acid or an organic acid.

The metal is preferably a polyvalent metal, and more preferably alkaline earth metals and zinc. Particularly preferred metals are calcium and zinc.

Inorganic acids that may be used in the metal salt formation include hydrogen halide (e.g., hydrochloric acid, hydrobromic acid, hydroiodic acid, hydrofluoric acid), sulfuric acid, nitric acid, thiocyanic acid, and so on.

Organic acids that may be used in the metal salt formation include aliphatic carboxylic acids and aromatic acids. Preferred aliphatic carboxylic acids are $C_{1-9}$ aliphatic carboxylic acids, e.g., aliphatic monocarboxylic acids, aliphatic dicarboxylic acids, and aliphatic tricarboxylic acids. The aliphatic carboxylic acids may be saturated or unsaturated.

The aliphatic monocarboxylic acids include $C_{1-9}$ saturated aliphatic monocarboxylic acids (e.g., carbonic acid, acetic acid, propionic acid, butyric acid, valeric acid, caproic acid, enanthoic acid, caprylic acid, pelargonic acid, capric acid, etc.) and $C_{2-9}$ unsaturated aliphatic monocarboxylic acids (e.g., acrylic acid, propiolic acid, methacrylic acid, crotonic acid, isocrotonic acid, etc.).

The aliphatic dicarboxylic acids include $C_{2-9}$ saturated aliphatic dicarboxylic acids (e.g., malonic acid, succinic acid, glutaric acid, adipic acid, pimellic acid, etc.) and $C_{2-9}$ unsaturated aliphatic dicarboxylic acids (e.g., maleic acid, fumaric acid, citraconic acid, mesaconic acid, etc.).

The aliphatic tricarboxylic acids include $C_{2-9}$ saturated aliphatic tricarboxylic acids (e.g., tricarvallylic acid, 1,2,3-butanetricarboxylic acid, etc.).

The above mentioned aliphatic carboxylic acids additionally may have 1 or 2 hydroxyl groups. Illustrative examples are glycolic acid, lactic acid, glyceric acid, tartronic acid, malic acid, tartaric acid, citric acid, and so on.

Preferred aliphatic carboxylic acids are aliphatic monocarboxylic acids. More preferred aliphatic carboxylic acids are $C_{2-9}$ aliphatic monocarboxylic acids. Particularly preferred are $C_{2-3}$ saturated aliphatic monocarboxylic acids. The most preferred aliphatic carboxylic acid includes acetic acid.

Aromatic acids that may be used in the metal salt formation include benzoic acid, salicylic acid and phenolsulfonic acid.

The metal salt of the biodegradable polymer, may also be obtained using the acetylacetonate or oxide of the above-mentioned polyvalent metals. Preferred metal donors of the type are zinc acetylacetonate and zinc oxide.

Metal salts which can be used for converting a biodegradable polymer to its metal salt are preferably the salt formed by a polyvalent metals with an organic or inorganic acid (hereinafter referred to as a polyvalent metal salt).

Polyvalent metal salt that may be used include salts of zinc with an inorganic acid, e.g., zinc halides (e.g. zinc chloride, zinc bromide, zinc iodide, zinc fluoride), zinc sulfate, zinc nitrate, zinc thiocyanate, etc.; salts of zinc with an organic acid, e.g., aliphatic carboxylic acid zinc salts (e.g. zinc carbonate, zinc acetate, zinc glycolate, zinc lactate, zinc tartrate, etc.), aromatic zinc salts (e.g. zinc benzoate, zinc salicylate, zinc phenolsulfonate, etc.); salts of calcium with an inorganic acid, e.g., calcium halide (e.g., calcium chloride, calcium bromide, calcium iodide, calcium fluoride, etc.), calcium sulfate, calcium nitrate, calcium thiocyanate, etc.; salts of calcium with an organic acid, e.g., aliphatic carboxylic acid calcium salt (e.g, calcium carbonate, calcium acetate, calcium propionate, calcium oxalate, calcium tartrate, calcium lactate, calcium citrate, calcium gluconate, etc.) and aromatic calcium salts (e.g. calcium benzoate, calcium salicylate, etc.).

The preferred polyvalent metal salt includes zinc acetate and calcium acetate.

The bioactive polypeptides used in the present invention include bioactive polypeptides having molecular weights from about 1,000 to about 50,000, preferably about 5,000 to about 40,000.

The representative activity of the bioactive peptide in the present invention is hormonal activity. The bioactive polypeptides may be natural products, synthetic products, semi-synthetic products, and their derivatives. The mode of action of the bioactive polypeptide may be agonistic or antagonistic.

The bioactive polypeptide for use in the present invention includes peptide hormones, cytokines, hematopoietic factors, various growth factors and enzymes.

The bioactive polypeptide hormones include insulin, growth hormone, naturiuretic peptides, gastrin, prolactin, adrenocorticotropic hormone (ACTH), thyroid stimulating hormone (TSH), luteinizing hormone (LH), follicle stimulating hormone (FSH), human chorionic gonadotropin (HCG) and motilin. The preferred hormones are insulin and growth hormone.

The bioactive polypeptide cytokines include lymphokines and monokines. The lymphokines includes interferons (alpha, beta and gamma) and interleukins (IL-2 to IL-12). The monokines includes interleukin-1 (IL-1), and tumor necrosis factor. The preferred cytokine is a lymphokine and, more preferred interferon. The particularly preferred cytokine is interferon-α.

The bioactive polypeptide hematopoietic factors include erythropoietin, granulocyte colony stimulating factor (G-CSF), macrophage colony stimulating factor (M-CSF), thrombopoietin, platelet-derived growth factor, and megakaryocyte potentiator.

The bioactive polypeptide growth factors include basic and acidic fibroblast growth factors (FGF) and their families (e.g., FGF-9), nerve growth factor (NGF) and its family, insulin-like growth factors (e.g. IGF-1, IGF-2, etc.) and bone morphogenetic protein (BMP) and family.

The bioactive polypeptide enzymes include superoxide dismutase (SOD), tissue plasminogen activator (TPA) and kallikrein.

When the bioactive polypeptide contains a metal, the metal content of the bioactive polypeptide in the present invention is preferably not greater than 0.1%, more preferably not greater than 0.01%, and most preferably not greater than 0.001%. Thus, substantially metal-free bioactive polypeptides are most suited for the present invention. Crystalline insulin, for instance, usually contains small amounts of heavy metals such as zinc, nickel, cobalt and cadmium. Insulin containing 0.4% (w/w) zinc exists as a stable hexamer and appears to be relatively inert in the interaction with the biodegradable polymer metal salt.

If necessary, the metals occurring in the bioactive polypeptide may be previously removed from the polypeptide by known methods. For example, one known method comprises dialyzing an aqueous hydrochlonic acid solution of insulin against water or an aqueous solution of ammonium acetate and lyophilizing the dialysate to provide amorphous insulin with minimal metal content.

In the present invention, it is preferable that additives other than the biodegradable polymer metal salt in the sustained-release preparation do not form a metal salt.

The biodegradable polymer metal salt in the present invention can be produced by emulsifing and dispersing an aqueous solution or solid form of a metal salt in an organic solvent solution of a biodegradable polymer to prepare a water/oil (w/o) or oil/water (o/w) emulsion or an organic solution or suspension of a biodegradable polymer containing a metal salt. The resulting substances are washed and dried or subjected to an in-water drying method, phase separation method, spray drying method or the like with washing and drying. The metal salt which does not participate in the formation of a salt with the biodegradable polymer in this process is preferably removed.

The organic solvent mentioned above preferably has a boiling point not exceeding 120° C. Such organic solvent includes halogenated hydrocarbons (e.g., dichloromethane, chloroform, carbon tetrachloride, etc.), alcohols (e.g. ethanol, methanol, etc.), acetonitrile, and so on. These solvents can also be used as a mixture. The preferred organic solvents are dichloromethane and acetonitrile. Particularly preferred is dichloromethane.

The metal content of the biodegradable polymer metal salt is preferably about 0.01 to about 10% (w/w), more preferably about 0.05 to about 7% (w/w), and most preferably about 0.1 to about 5% (w/w). The metal content of a biodegradable polymer metal salt can be determined by atomic absorption spectrometry.

Methods for producing a biodegradable polymer metal salt (e.g., in-water drying method, phase separation method and spray drying method) are described below.

(A) In-water Drying Method (Water/Oil/Water or W/O/W Method)

In this method, the biodegradable polymer is first dissolved in an organic solvent to prepare an organic solvent solution (hereinafter referred to sometimes as the oil phase). The concentration of the biodegradable polymer in this organic solvent solution is suitably selected according to the molecular weight of the polymer and the kind of organic solvent used. For example, the concentration of the biodegradabe polymer in the organic solvent may be about 0.01 to about 90% (w/w), preferably about 0.1 to about 80% (w/w), and more preferably about 1 to about 70% (w/w). For the internal aqueous phase, an aqueous solution of metal salts is used. The metal salt concentration may be from about 10 to about 90% (w/v), and preferably about 20 to about 80% (w/v). However, the metal salt concentration depends on the solubility of the metal salt in water. The above metal salt aqueous solution is dispersed and emulsified in the organic solvent solution of the biodegradable polymer to provide a w/o emulsion. The volume ratio of the aqueous solution of metal salts in the organic solvent solution of the biodegradable polymer is about 1:1,000 to about 1:1, preferably about 1:100 to about 1:2, and most preferably about 1:50 to about 1:3. Emulsification can be achieved by conventional emulsification methods such as by using a turbine mixer, a homogenizer or the like.

The w/o emulsion thus obtained is then added to an aqueous phase (the external aqueous phase) to give a w/o/w emulsion. Then the oil-phase solvent is evaporated off to provide the desired biodegradable polymer metal salt. The volume of the external aqueous phase may be selected from the range of, for example, about 1 to about 10,000 times the volume of the oil phase. The preferred range is about 2 to about 5,000 times, and the most preferred range is about 5 to about 2,000 times. Solvent evaporation can be achieved by commonly used methods, including the method in which the solvent is evaporated under normal or gradually reduced pressure while stirring using a propeller stirrer or a magnetic stirrer, etc., and the method in which the solvent is evaporated while the degree of vacuum is adjusted using a rotary evaporator, and so on.

An emulsifier may be added to the external aqueous phase. The emulsifier may be any substance capable of providing for stable w/o/w emulsions. Examples of such emulsifiers include anionic surfactants, nonionic surfactants, polyoxyethylene-castor oil derivatives, polyvinylpyrrolidone, polyvinyl alcohol, carboxymethylcellulose, lecithin, gelatin, hyaluronic acid and so on. The preferred emulsifier is polyvinyl alcohol. Multiple emulsifiers may also be used in combination for use in the external aqueous phase. The concentration of the emulsifier based on the external aqueous phase may be selected from the range of about 0.001 to about 20% (w/w). The preferred range is about 0.01 to about 10% (w/w) and the still more preferred range is about 0.05 to about 5% (w/w).

A metal salt which is similar to or different from the metal salt contained in the internal aqueous phase may also be added to the external aqueous phase. In such cases, preferably a fatty acid metal salt is added in such an amount that the concentration of the metal salt in the external aqueous phase is about 0.01 to 20% (w/w) or more preferably about 0.1 to 10% (w/w). By careful selection of the concentration of the metal salt in the external aqueous phase, the transfer of the metal salt used in the internal aqueous phase from the biodegradable polymer into the external aqueous phase may be avoided.

The biodegradable polymer metal salt thus produced is recovered by centrifugation or filtration, washed with distilled water several times to remove the emulsifier and other deposits from the salt surface, then redispersed in distilled water, and lyophilized.

(B) In-water Drying Method (O/W Method)

In this process, a solution of the biodegradable polymer in an organic solvent is first prepared as in method (A).

Then, the metal salt is added, and dispersed or dissolved in the organic solvent solution of biodegradable polymer. The ratio of metal salt to biodegradable polymer (by weight) is about 5:1 to about 1:100, preferably about 2:1 to about 1:50, and more preferably about 1:1 to about 1:10.

The organic solvent solution thus obtained is then poured into an aqueous phase and an o/w emulsion is prepared by using a turbine mixer or the like. Then, the oil-phase solvent is evaporated as in method (A) to provide the biodegradable polymer metal salt. The volume of the aqueous phase is based on the volume of oil phase and is selected from the range of, for example, about 1 to about 10,000 times the volume of the oil phase, or preferably about 2 to about 5,000 times. The most preferred range is about 5 to about 2,000 times.

As in method (A), an emulsifier may be added into this aqueous phase.

A metal salt may be added into the aqueous phase that is similar to or different from the metal salt which is added, and dispersed or dissolved in the oil phase.

The biodegradable polymer metal salt thus produced is separated, washed and lyophilized as in method (A).

(C) Phase Separation Method (Coacervation Method)

For the production of a biodegradable polymer metal salt by this method, a coacervating agent is gradually added into the w/o emulsion as used in method (A) or the organic solvent solution of biodegradable polymer containing the metal salt as used in method (B) under stirring to precipitate and solidify the biodegradable polymer metal salt. The amount of coacervating agent used is based on the volume of the w/o emulsion or organic solvent solution of the biodegradable polymer. The volume used is about 0.01 to about 1,000 times the volume of the W/O emulsion or organic solution of the biodegradable polymer, preferably about 0.05 to about 500 times, and more preferably about 0.1 to about 200 times.

The coacervating agent may be a substance belonging to any of the categories of polymers, mineral oils or vegetable oils, which are miscible with the organic solvent used for dissolving the biodegradable polymer, but in which the biodegradable polymer is not appreciably soluble. Typical examples are silicone oil, sesame oil, soybean oil, corn oil, cottonseed oil, coconut oil, linseed oil, mineral oil, n-hexane, n-heptane, and so on. The coacervating agents can be used in a combination of two or more kinds.

The biodegradable polymer metal salt thus produced is recovered by filtration and washed repeatedly with heptane or the like to remove the coacervating agent. The salt is then washed as in method (A) and lyophilized.

In the production of a biodegradable polymer metal salt by the in-water drying method or coacervation method, an antiflocculant may be added for preventing agglomeration of the particles. Antiflocculants that may be used includ a water-soluble polysaccharides, such as mannitol, lactose, glucose, and starches (e.g. corn starch), hyaluronic acid and its alkali metal salt, glycine, a protein such as fibrin, collagen and an inorganic salt such as sodium chloride, sodium hydrogen phosphate, and so on.

(D) Spray Drying Method

For the production of a biodegradable polymer metal salt by this method, either a w/o emulsion prepared from an aqueous solution of the metal salt and an organic solvent solution of the biodegradable polymer, or an organic solvent solution or suspension of biodegradable polymer containing the metal salt, is sprayed via a nozzle into the drying chamber of a spray drier to volatilize the organic solvent in fine droplets in a very short time, and a fine biodegradable polymer metal salt is produced. Examples of the abovementioned nozzle are a binary-fluid nozzle, a pressure nozzle and a rotary disk nozzle. An aqueous solution of the above-described antiflocculant also may be sprayed via another nozzle in order to prevent agglomeration of biodegradable polymer metal salt with the w/o emulsion or the organic solvent solution or suspension of the biodegradable polymer containing the metal salt. The biodegradable polymer metal salt thus produced is washed as in method (A) and, if necessary, further subjected to removal of water and organic solvent under heating and reduced pressure.

The sustained-release preparation of the present invention can be manufactured by dispersing a bioactive polypeptide in an organic solvent containing the biodegradable polymer metal salt, and subjecting the resulting dispersion to formulation. The manufacturing method of the present invention can be used with the above-described (A) in-water drying method (w/o/w method), (B) in-water drying method (o/w method), (C) phase separation method (coacervation method), (D) spray drying method, or any modification thereof. The organic solvent in the organic solvent solution is preferably a solvent with a boiling point not higher than 120° C. Such organic solvent includes halogenated hydrocarbons (e.g., dichloromethane, chloroform, carbon tetrachloride, etc.), alcohols (e.g., ethanol, methanol, 1,4-butanediol, 1,5-pentanediol, etc.) and acetonitrile, among others. Any of the solvents can be used together as a mixture. When a single organic solvent is to be employed, dichloromethane or acetonitrile is particularly preferred. When a mixture of organic solvents is to be employed, a combination of a halogenated hydrocarbon (e.g., dichloromethane) with acetonitrile or an alcohol (e.g., methanol, ethanol, etc.) is preferred. Particularly preferred in many instances is a combination of dichloromethane with acetonitrile. The ratio (by volume) of the halogenated hydrocarbon to either acetonitrile or alcohol is about 40:1 to about 1:1 and preferably about 20:1 to about 1:1.

The manufacturing method for sustained-release preparation is now described using microcapsules as an example.

(i) In-water Drying Method (W/O/W Method)

In this process, an organic solvent solution of the biodegradable polymer metal salt is first prepared in the same manner as in method (A) described above. The concentration of the biodegradable polymer metal salt in the organic solvent solution is dependent on the type and molecular weight of biodegradable polymer metal salt and the type of the organic solvent. For example, the ratio of biodegradable polymer metal salt to organic solvent may be about 0.01 to about 80% (w/w), and is preferably about 0.1 to about 70% (w/w), and most preferably about 1 to about 60% (w/w). For the internal aqueous phase, an aqueous solution of the bioactive polypeptide is used. The concentration of the bioactive polypeptide in aqueous solution may be for example, about 0.1% (w/v) to about 500% (w/v), preferably about 1% (w/v) to about 400% (w/v) and more preferably about 10% (w/v) to about 300% (w/v). To this aqueous solution may be added pH adjusting agent (e.g., acetic acid, hydrochloric acid, sodium hydroxide, etc.), stabilizers (e.g., serum albumin, gelatin, etc.), and/or preservatives (e.g., p-hydroxybenzoic acid esters, etc.). The aqueous solution thus obtained is dispersed in the organic solvent solution of biodegradable polymer metal salt to provide a w/o emulsion.

The ratio (v/v) of aqueous solution of bioactive polypeptide to organic solvent solution of biodegradable polymer metal salt is about 1:1,000 to about 1:1, preferably about 1:100 to about 1:5, and more preferably about 1:50 to about 1:5. The w/o emulsion thus obtained is then poured in an aqueous phase (external aqueous phase) to give a w/o/w emulsion and the solvent in the oil phase is evaporated to provide microcapsules. An emulsifier may be added to the external aqueous phase. The emulsifier can be any substance that is generally capable of providing a stable w/o/w emulsion. Specifically, anionic surfactants, nonionic surfactants, polyoxyethylene-castor oil derivatives, polyvinylpyrrolidone, polyvinyl alcohol, carboxymethylcellulose, lecithin, gelatin, hyaluronic acid, etc. may be employed. The preferred emulsifier is polyvinyl alcohol. Two or more kinds of emulsifiers can be used in combination. The concentration of the emulsifier based on the external aqueous phase is chosen from a range of about 0.001% (w/w) to about 20% (w/w), preferably about 0.01% (w/w) to about 10% (w/w), and more preferably about 0.05% (w/w) to about 5% (w/w). A metal salt, whether the same salt as that added to the internal aqueous phase or a different salt, can be added to the external aqueous phase. In this procedure, preferably a fatty acid metal salt is added so that the metal salt concentration of the external aqueous phase will be about 0.01% to about 20% (w/w) and preferably about 0.1% to about 10% (w/w). By changing the metal salt concentration of the external aqueous phase, the metal salt used in the internal aqueous phase can be prevented from migrating from the biodegradable polymer into the external aqueous phase.

The microcapsules thus produced are recovered by centrifugation or filtration, washed with distilled water repeatedly to remove the emulsifier and other deposits from the capsule surface, then redispersed in distilled water or the like, and lyophilized. Then, if necessary, residual water and organic solvent in the microcapsules are further removed by heating under reduced pressure. The microcapsules are heated at a temperature not below the glass transition temperature of the biodegradable polymer and not so high as to cause aggregation of the microcapsules. The heating temperature is preferably selected within the range from the glass transition temperature of the biodegradable polymer to about 30° C. higher than the glass transition temperature of the biodegradable polymer. Here, glass transition temeraiture is defined as the intermediate glass transition temperature determined using a differential scanning calorimeter during heating at a rate of 10 or 20° C. per minute.

(ii) In-water Drying Method (O/w Method)

In this process, an organic solvent solution of the biodegradable polymer metal salt is first prepared in the same manner as in method (A). The concentration of the biodegradable polymer metal salt in the organic solvent may be similar to that described in method (i). In the organic solvent solution of the biodegradable polymer metal salt thus obtained is added and dissolved or dispersed a bioactive polypeptide to prepare an organic solvent solution or suspension containing the biodegradable polymer metal salt and bioactive polypeptide. The weight ratio of the bioactive polypeptide to the biodegradable polymer metal salt may for example be about 1:1000 to about 1:1, preferably about 1:200 to about 1:5 and more preferably about 1:100 to about 1:5.

This organic solvent solution containing the biodegradable polymer metal salt and bioactive polypeptide is poured into an aqueous phase to prepare an o/w emulsion. The solvent in the oil phase is then evaporated off to provide microcapsules.

The microcapsules thus obtained are recovered, washed and lyophilized as in method (i). Thereafter the microcapsules may be heated under reduced pressure to remove the residual water and organic solvent as in method (i).

(iii) Phase Separation Method

In the production of microcapsules by this method, a coacervating agent is gradually added to the same w/o emulsion as used in method (i) or the same organic solvent solution of biodegradable polymer metal salt and bioactive polypeptide as used in method (ii) under stirring in the same manner as in method (C) to afford precipitated and solidified microcapsules.

The microcapsules thus produced are recovered and washed to remove the coacervating agent and free bioactive polypeptide as in method (C). Then, if necessary, the residual water and organic solvent within the microcapsules are removed by heating under reduced pressure in the same manner as in method (i).

In the production of microcapsules by the in-water drying method or phase separation method, an antiflocculant may be added for preventing agglomeration of particles as in method (C).

(iv) Spray-drying Method

In the production of microcapsules by this method, the same w/o emulsion as used in method (i) or the same organic solvent solution containing the biodegradable polymer metal salt and bioactive polypeptide as used in method (ii) is sprayed via a nozzle in the same manner as in method (D) to provide microcapsules.

If necessary, the microcapsules thus obtained are heated under reduced pressure to remove residual water and organic solvent as in method (i).

In the present invention, it is preferable that the efficiency of entrapment of a bioactive polypeptide into a biodegradable polymer is over 50%.

The concentration of bioactive polypeptide comprised in the sustained-release preparation in the present invention is, for example, about 0.001 to about 30% (w/w), preferably about 0.02 to about 20% (w/w), more preferably about 0.1 to about 10% (w/w), and most preferably about 0.5 to about 5% (w/w).

The sustained-release preparation may be administered in the form of microcapsule or in various dosage forms such as non-oral preparations (e.g., intramuscular-, subcutaneous- or visceral-injectable or indwellable preparation; nasal-, rectal or uterine-transmucosal preparation), or oral preparations (e.g., capsules such as hard capsule and soft capsule, solid preparations such as in granules and powder, liquid preparations such as a suspension).

The particularly preferred sustained-release preparation is by injection. To prepare an injection using the microcapsules obtained above, the microcapsules may be formulated with a dispersant (e.g., surfactants such as Tween 80, HCO-60; polysaccharides such as carboxymethylcellulose, sodium alginate, sodium hyaluronate; protamine sulfate; polyethylene glycol 400, etc.), a preservative (e.g., methyl paraben, propyl paraben, etc.), an isotonizing agent (e.g., sodium chloride, mannitol, sorbitol, glucose, etc.), and a local anesthetic (e.g., xylocaine hydrochloride, chlorobutanol, etc.) to provide an aqueous suspension, or dispersed with vegetable oil (e.g., sesame oil, corn oil, etc.), or a mixture thereof with a phospholipid (e.g., lecithin) or medium-chain fatty acid triglycerides (e.g., Migriol 812) to provide an oily suspension.

When the sustained-release preparation is microcapsules, the microcapsules are preferably fine particle. The size of microcapsules for an injectable suspension may be selected from the range satisfying the requirements for the degree of dispersion and passage through the needle used for the injection. For example, the microcapsul perticle size may be within the range of about 0.1 to about 300 $\mu$m, preferably about 1 to about 150 $\mu$m and more preferably about 2 to about 100 $\mu$m.

Methods of preparing microcapsules as a sterile preparation include, but are not limited to, the method in which the entire production process is sterile, the method in which gamma rays are used as the sterilant, and method in which an antiseptic is added during the manufacturing process.

The sustained-release preparation can be safely used in mammals (e.g., humans, bovine, swine, dogs, cats, mice, rats, rabbits, etc.) with low toxicity.

The specific application of the sustained-release preparation varies from kinds of the bioactive polypeptides.

For example, sustained-release preparation is useful to prevent or treat diabetes when insulin is used as bioactive the polypeptide; growth hormone hyposecretion and Turner's syndrome when growth hormone is used; viral hepatitis (e.g., type C hepatitis, HBe antigen-positive active heptitis) and cancer (e.g., renal carcinoma, multiple myeloma, etc.) when interferon-$\alpha$ is used; anemia (e.g., anemia during a dialysis of kidney) when erythropoietin is used; neutropenia (e.g., in therapy of carcinostatic) and infections when G-CSF is used; cancer (e.g., hemangioendothelioma) when IL-2 is used; gastrointestinal ulcer when FGF-9 is used; senile dementia and neuropathy when NGF is used; thrombosis when TPA is used; and cancer when tumor recrosis factor is used.

Dosage of the sustained-release preparation is the effective concentration of the bioactive polypeptide in vivo, though the dosage varies with the type of the bioactive polypeptide, the desired duration of the release, the target disease, the subject animal species and the other factors.

When the sustained-release preparation is a one-week-long action formulation, the dosage of the bioactive polypeptide can be chosen from the range of about 0.0001 to about 10 mg/kg body weight per an adult. The more preferred dosage can be suitably chosen from the range of about 0.0005 to about 1 mg/kg body weight. The preferred administration frequency of the sustained-release preparation may be suitably chosen from once a week to once every two weeks depending on the type of bioactive polypeptide, the dosage form, the duration of the release, the target disease, the subject animal species and other factors.

For example, when insulin is the bioactive polypeptide contained in the sustained-release preparation, the dosage for an adult diabetic can be usually selected from the range of about 0.001 to about 1 mg (as active ingredient)/kg body weight and preferably from the range of about 0.01 to about 0.2 mg/kg body weight with the dosage form to be administered on a weekly basis. In the case of growth hormone, the dosage for a patient with pituitary dwarfism is chosen from the range of about 0.004 mg to about 4 mg/kg body weight and preferably about 0.04 mg to about 0.8 mg/kg body weight as the active ingredient and is preferably administered at one-week intervals. Alternatively, the dosage can be chosen from a range of about 0.008 mg to about 8 mg/kg body weight and preferably about 0.08 mg to about 1.6 mg/kg body weight, for administration every 2 weeks.

The sustained-release preparation is preferably stored at room temperature or in the cold. More preferably, the sustained-release preparation is stored in the cold. "Room temperature" means 15° to 25° C., and "cold" means a temperature below 15° C.

BEST MODE FOR CARRYING OUT THE INVENTION

The following reference examples and working examples are intended to describe the present invention in further detail and should not be construed as limiting the scope of the invention.

Reference Example 1

4 g of lactic acid-glycolic acid copolymer (lactic acid/glycolic acid=50/50 (mol %), weight average molecular weight 6000) was dissolved in 4 ml of dichloromethane. To this solution was added 1 ml of 438 mg/ml aqueous zinc acetate solution and the mixture was agitated in a bench-top homogenizer to prepare a w/o emulsion. This emulsion was poured into 800 ml of a 0.1% (w/v) aqueous polyvinyl alcohol (PVA) solution, the temperature of which was pre-adjusted to 18° C., and using a turbine homo-mixer, a w/o/w emulsion was prepared. Then, with this w/o/w emulsion being agitated at room temperature, the dichloromethane was evaporated off to produce a lactic acid-glycolic acid copolymer zinc salt. This lactic acid-glycolic acid copolymer zinc salt was recovered by centrifugation (about 1000 rpm) and the supernatant was discarded. The pellet was washed with 600 ml of distilled water twice and lyophilized to provide a powder of lactic acid-glycolic acid copolyme zinc salt. The zinc content of this salt as measured by atomic absorption spectrometry was 1.36% (w/w).

Reference Example 2

4 g of lactic acid-glycolic acid copolymer (lactic acid/glycolic acid=50/50 (ml %), weight average molecular weight 10000) was dissolved in 4 ml of dichloromethane. To this solution was added 1.5 ml of 292 mg/ml aqueous zinc acetate solution and the mixture was agitated in a bench-top homogenizer to prepare a w/o emulsion. This emulsion was treated in the same manner as in Reference Example 1 to provide a powder of lactic acid-glycolic acid copolymer zinc salt. The zinc content of this salt as measured by atomic absorption spectrometry was 1.1% (w/w).

Reference Example 3

4 g of lactic acid-glycolic acid copolymer (lactic acid/glycolic acid=50/50 (mol %), weight average molecular weight 15000) was dissolved in 4 ml of dichloromethane. To this solution was added 1.5 ml of 292 mg/ml aqueous zinc acetate solution and the mixture was agitated in a bench-top homogenizer to prepare a w/o emulsion. This emulsion was treated as in Reference Example 1 to provide a powder of lactic acid-glycolic acid copolymer zinc salt. The zinc content of this salt as measured by atomic absorption spectrometry was 0.99%.

Reference Example 4

1 g of recombinant human insulin (Wako Pure Chemical Industries, zinc content 0.35%) was dissolved in 200 ml of 0.01N-hydrogen chloride solution. Then, using a semipermeable membrane with a molecular weight of 6000 cut-off (Spectrapor™ 7 MWCO 1000, Spectrum Medical Industries, U.S.A.), the above solution was dialyzed against 10 L of 0.01N hydrogen chloride solution 3 times. The dialysate was further dialized against 30 L of 0.2M aqueous ammonium acetate solution once, 30 L of distilled water once and, then, lyophilized. The zinc content of the lyophilized insulin powder was less than 0.0001% (w/w).

Reference Example 5

8 g of lactic acid-glycolic acid copolymer (lactic acid/glycolic acid=50/50 (mol %), weight average molecular weight 6000) was dissolved in 8 ml of dichloromethane. To this solution was added 1.5 ml of 292 mg/ml aqueous zinc acetate solution and using a bench-top homogenizer, a w/o emulsion was prepared. This emulsion was added to 1800 ml of 0.1% (w/v) aqueous polyvinyl alcohol solution which had been preadjusted to 18° C., and using a turbine homogenizer, a w/o/w emulsion was prepared. This emulsion was treated as in Reference Example 1 to provide a powdery lactic acid-glycolic acid copolymer zinc salt. As determined by atomic absorption spectrometry, the zinc content of this lactic acid-glycolic acid copolymer zinc salt was 1.15%.

Reference Example 6

8 g of lactic acid-glycolic acid copolymer (lactic acid/glycolic acid=50/50 (mol %), weight average molecular weight 6000) was dissolved in 8 ml of dichloromethane. To this solution was added 1.5 ml of 292 mg/ml aqueous zinc acetate solution, and using a bench-top homogenizer, a w/o emulsion was prepared. This emulsion was treated as in Reference Example 4 to provide a powdery lactic acid-glycolic acid copolymer zinc salt. As determined by atomic absorption spectrometry, the zinc content of this lactic acid-glycolic acid copolymer zinc salt was 1.24%.

Reference Example 7

8 g of lactic acid-glycolic acid copolymer (lactic acid/glycolic acid=50/50 (mol %), weight average molecular weight 15000) was dissolved in 8 ml of dichloromethane. To this solution was added 1.2 ml of 292 mg/ml aqueous zinc acetate solution, and using a bench-top homogenizer, a w/o emulsion was prepared. This emulsion was treated as in Reference Example 4 to provide a powdery lactic acid-glycolic acid copolymer zinc salt. As determined by atomic absorption spectrometry, the zinc content of this lactic acid-glycolic acid copolymer zinc salt was 0.96%.

Reference Example 8

8 g of lactic acid-glycolic acid copolymer (lactic acid/glycolic acid=50/50 (mol %), weight average molecular weight 8000) was dissolved in 8 ml of dichloromethane. To this solution was added 1.5 ml of 292 mg/ml aqueous zinc acetate solution, and using a bench-top homogenizer, a w/o emulsion was prepared. This emulsion was added to 1800 ml of 0.1% (w/v) aqueous polyvinyl alcohol solution which had been preadjusted to 18° C., and using a turbine homogenizer, a w/o/w emulsion was prepared. Then, while stirring the w/o/w emulsion at room temperature, the dichloromethane solvent was evaporated off to give a lactic acid-glycolic acid copolymer zinc salt. This lactic acid-glycolic acid copolymer zinc salt was harvested by centrifugation (about 1000 rpm) and the supernatant was discarded. The salt was rinsed with 1200 ml of distilled water twice. This procedure was repeated a second time and the second crop was combined with the first crop, and the mixture was lyophilized to provide 11.8 g of lactic acid-glycolic acid copolymer zinc salt in a powdery form. As determined by atomic absorption spectrometry, the zinc content of this lactic acid-glycolic acid copolymer zinc salt was 1.19% (w/w).

EXAMPLE 1

900 mg of the lactic acid-glycolic acid copolymer zinc salt obtained in Reference Example 1 was dissolved in 1 ml of dichloromethane. To this solution was added 100 mg of the lyophilized Zn-free insulin powder prepared in Reference Example 4 and the mixture was agitated in a bench-top homo-mixer to prepare an organic solvent solution containing both the insulin and the lactic acid-glycolic acid copolymer zinc salt. This organic solvent solution was poured in 800 ml of 0.1% (w/v) aqueous polyvinyl alcohol (PVA) solution preadjusted to 18° C. and using a turbine homogenizer, an o/w emulsion was prepared. Then, while the o/w emulsion was agitated at room temperature, the dichloromethane was evaporated off to provide microcapsules. The microcapsules were recovered by centrifugation (about 1000 rpm) and the supernatant was discarded. The pellet was rinsed with 600 ml of distilled water twice and lyophilized to provide 520 mg of powdery insulin-containing microcapsules.

EXAMPLE 2

900 mg of the lactic acid-glycolic acid copolymer zinc salt prepared in Reference Example 2 was dissolved in 1 ml of dichloromethane. To this solution was added 100 mg of the lyophilized Zn-free insulin powder obtained in Reference Example 4 and the mixture was treated as in Example 1 to provide 450 mg of powdery insulin-containing microcapsules.

EXAMPLE 3

900 mg of the lactic acid-glycolic acid copolymer zinc salt prepared in Reference Example 3 was dissolved in 1.5 ml of dichloromethane. To this solution was added 100 mg of the lyophilized Zn-free insulin powder obtained in Reference Example 4 and the mixture was treated as in Example 1 to provide 503 mg of powdery insulin-containing microcapsules.

EXAMPLE 4

950 mg of the lactic acid-glycolic acid copolymer zinc salt prepared in Reference Example 1 was dissolved in 1.5 ml of dichloromethane. To this solution was added the powder from 8 vials (128 IU) of human growth hormone (Genotropin™ 16IU/ampule, Sumitomo pharmaceutical Company Limited) and the mixture was treated as in Example 1 to provide 500 mg of growth hormone-containing microcapsules.

EXAMPLE 5

950 mg of the lactic acid-glycolic acid copolymer zinc salt obtained in Reference Example 5 was dissolved in 1.5 ml of dichloromethane. To this solution was added 50 mg of lyophilized human growth hormone powder and the mixture was treated as in Example 1 to provide 517 mg of powdery growth hormone-containing microcapsules.

EXAMPLE 6

950 mg of the lactic acid-glycolic acid copolymer zinc salt obtained in Reference Example 3 was dissolved in 3 ml of dichloromethane. To this solution was added 50 mg of lyophilized human growth hormone powder and the mixture was treated as in Example 1 to provide 415 mg of powdery growth hormone-containing microcapsules.

EXAMPLE 7

475 mg of the lactic acid-glycolic acid copolymer zinc salt obtained in Reference Example 6 and 475 mg of lactic acid-glycolic acid copolymer (lactic acid/glycolic acid=50/50 (mol %), weight average molecular weight 6000) were dissolved in 1.5 ml of a mixture of dichloromethane and ethanol (dichloromethane/ethanol=2/1 (v/v)). To this solution was added 50 mg of lyophilized human growth hormone powder and the mixture was treated as in Example 1 to provide 249 mg of powdery growth hormone-containing microcapsules.

EXAMPLE 8

475 mg of the lactic acid-glycolic acid copolymer zinc salt obtained in Reference Example 7 and 475 mg of lactic acid-glycolic acid copolymer (lactic acid/glycolic acid=50/50 (mol %), weight average molecular weight 15000) were dissolved in 3 ml of dichloromethane-ethanol (2/1, v/v). To this solution was added 50 mg of lyophilized human growth hormone powder and the mixture was treated as in Example 1 to provide 447 mg of powdery growth hormone-containing microcapsules.

EXAMPLE 9

2.12 g of the lactic acid-glycolic acid copolymer zinc salt obtained in Reference Example 8 was dissolved in 3.45 ml of dichloromethane. Then, 160 mg of the lyophilized zinc-free insulin powder obtained in Reference Example 4 was added to 2 ml of dichloromethane and sonicated for 5 minutes to prepare an insulin suspension. To this suspension was added the above dichloromethane solution of lactic acid-glycolic acid copolymer zinc salt (corresponding to 1.84 g of lactic acid-glycolic acid copolymer zinc salt). The mixture was treated with a vortex mixer and, then, with a bench-top homogenizer to give an organic solvent solution containing both insulin and lactic acid-glycolic acid copolymer zinc salt. This organic solvent solution was added to 2000 ml of a 0.1% (w/v) aqueous polyvinyl alcohol solution containing 1.4% of zinc acetate dihydrate preadjusted to 18° C., and using a turbine homomixer, an o/w emulsion was prepared. Then, while the o/w emulsion was agitated at room temperature, the dichloromethane was evaporated off to provide microcapsules. The microcapsules were harvested by centrifugation (about 1000 rpm) and the supernatant was discarded. The microcapsules were rinsed with 1200 ml of distilled water twice, and after addition of 250 mg of mannitol, they were lyophilized to provide 1.53 g of powdery insulin-containing microcapsules.

EXAMPLE 10

1.06 g of the lactic acid-glycolic acid copolymer zinc salt obtained in Reference Example 8 was dissolved in 2.3 ml of dichloromethane/acetonitrile (10/1, v/v). Meanwhile, 80 mg of the lyophilized zinc-free insulin powder obtained in Reference Example 4 was added to 1 ml of dichloromethane/acetonitrile (10/1, v/v) and sonicated for 5 minutes to prepared an insulin suspension. To this suspension was added the above dichloromethane solution of lactic acid-glycolic acid copolymer zinc salt (corresponding to 0.92 g of lactic acid-glycolic acid copolymer zinc salt) and the mixture was processed with a vortex mixer and further with a bench-top homogenizer to prepare an organic solvent solution containing both insulin and the lactic acid-glycolic acid copolymer zinc salt. This organic solvent solution was added to 1000 ml of a 0.1% (w/v) aqueous polyvinyl alcohol solution containing 0.7% (w/v) of zinc acetate dihydrate, which had been preadjusted to 18° C., and using a turbine homogenizer, an o/w emulsion was prepared. While the o/w emulsion was agitated at room temperature, the dichloromethane was evaporated off to provide microcapsules. The microcapsules were harvested by centrifugation (about 1000 rpm) and the supernatant was discarded. The microcapsules were washed with 600 ml of distilled water twice, followed by addition of 100 mg of mannitol and lyophilization to provide 0.734 g of powdery insulin-containing microcapsules.

Experimental Example 1

147 mg of the insulin-containing microcapsules prepared in Example 1 was dispersed in 1.75 ml of dispersion medium (mannitol 5% (w/v), carboxymethylcellulose 0.5% (w/v), Tween 20 0.1% (w/v), adjusted to pH 6.8 with acetic acid). A 0.5 ml portion (insulin content 100 U) of this dispersion was injected subcultaneously at the back of streptozocin-induced hyperglycemic rats under ether anesthesia. Blood was serially drawn from the tail vein and the serum was separated. The concentration of insulin in each serum sample was determined by enzyme immunoassay using the two-antibody sandwich method. As controls, insulin solution and Novolin™ U (Novo-Nordisk, Denmark), a commercial insulin delayed action preparation, (both containing 100 U insulin equivalent) were administered. The results are shown in Table 1. Thus, the serum insulin concentration in the insulin zinc-containing microcapsule treatment group was significantly well-sustained as compared with insulin solution and Novolin™ U, indicating that the sustained dosage form prepared by the method of the present invention has improved sustained-release characteristics.

TABLE 1

Time courses of blood insulin concentration after administration of various insulin preparations

| Insulin preparation | Blood concentration (µU/ml) | | | | | | | |
|---|---|---|---|---|---|---|---|---|
| | 0.5 hr. | 1 hr. | 2 hr. | 4 hr. | 8 hr. | 24 hr. | 48 hr. | 72 hr. |
| Insulin solution | 33,600 | 50,000 | 47,500 | 700 | 130 | <10 | <10 | <10 |
| Novolin U | 14 | 569 | 1,830 | 39,500 | 3,600 | 18 | <10 | <10 |
| Microcapsule | 55 | 485 | 1,370 | 11,400 | 4,630 | 3,630 | 601 | 47 |

Experimental Example 2

261 mg of the growth hormone-containing microcapsules obtained in Example 6 was dissolved in 1.75 ml of dispersion medium. A 0.5 ml portion of the dispersion (corresponding to 3 mg of growth hormone) was administered subcutaneously at the back of rats under ether anesthesia. As a control, a solution of growth hormone (containing 3 mg of growth hormone) was similarly administered. Blood was drawn serially from the tail vein and the serum was separated. The concentration of growth hormone in each serum sample was determined by radioimmunoassay (Ab Bead HGH, Eiken Kagaku). The results are presented in Table 2. Thus, the serum growth hormone concentration was sustained significantly longer in the growth hormone/zinc-containing microcapsule group, compared with the growth hormone solution group, suggesting an outstanding prolonged action characteristic of the sustained release dosage form manufactured by the method of the present invention.

Experimental Example 3

211 mg of the growth hormone-containing microcapsules obtained in Example 7 was dissolved in 1.75 ml of dispersion medium. A 0.5 ml portion of this dispersion (containing 3 mg of growth hormone) was administered subcutaneously at the back of ether-anesthetized rats. Blood was drawn serially from the tail vein and the serum separated. The concentration of growth hormone in each serum sample was determined by radioimmunoassay (Ab Bead HGH, Eiken Kagaku). The results are presented in Table 2. Thus, the serum growth hormone concentration in the growth hormone/zinc-containing microcapsule group was sustained significantly longer compared with the growth hormone solution group, with a marked suppression of initial release bursts, therefore suggesting an outstanding prolonged action characteristic of the sustained release dosage form manufactured by the method of the present invention.

TABLE 2

Time courses of blood growth hormone concentration after administration of various growth hormone preparations

| Growth hormone preparation | Blood concentration (ng/ml) | | | | | | | | |
|---|---|---|---|---|---|---|---|---|---|
| | 1 hr. | 2 hr. | 8 hr. | 1 day | 2 day | 3 day | 4 day | 5 day | 7 day |
| Growth hormone solution | 7,796 | 3,462 | 45 | 1 | N.D. | N.D. | N.D. | N.D. | N.D. |
| Microcapsule of Example 2 | 688 | 1,234 | 265 | 8 | 25 | 13 | 16 | 17 | 14 |
| Microcapsule of Example 3 | 12 | 55 | 8 | 4 | 2 | 4 | 3 | — | 6 |

Experimental Example 4

236.6 mg of the insulin-containing microcapsules obtained in Example 9 was dissolved in 1.75 ml of dispersion medium. A 0.5 ml portion (containing 100 U of insulin) of this dispersion was administered subcutaneously at the back of ether-anesthetized rats. Blood was drawn serially from the tail vein and the serum separated. Insulin concentration in each serum sample was determined by enzyme-linked immunosorbent assay. The results are presented in Table 3. Thus, the serum insulin concentration in the insulin/zinc-containing microcapsule group was sustained significantly longer compared with the insulin solution group, with marked inhibition of initial release bursts, suggesting an outstanding prolonged action characteristic of the sustained release dosage form manufactured by the method of the present invention.

Experimental Example 5

216.4 mg of the insulin-containing microcapsules obtained in Example 10 was dissolved in 1.75 ml of dispersion medium. A 0.5 ml portion (containing 100 U of insulin) of the above dispersion was administered subcutaneously at the back of ether-anesthetized rats. Blood was drawn serially from the tail vein and the serum separated. The concentration of insulin in each serum sample was determined by enzyme-linked immunosorbent assay. The results are presented in Table 3. Thus, the serum insulin concentration in the insulin/zinc-containing microcapsule group was sustained significantly longer compared with the insulin solution group, with marked inhibition of initial release bursts, suggesting an outstanding prolonged action characteristic of the sustained release dosage form manufactured by the method of the invention.

TABLE 3

Time courses of blood insulin concentration after administration of various insulin preparations

| Insulin preparation | Blood concentration ($\mu$U/ml) | | | | | | | | | |
|---|---|---|---|---|---|---|---|---|---|---|
| | 1 hr. | 2 hr. | 8 hr. | 1 day | 2 day | 3 day | 4 day | 5 day | 6 day | 7 day |
| Insulin solution | 50,000 | 47,500 | 130 | N.D. | N.D. | N.D. | N.D. | N.D. | N.D. | N.D. |
| Microcapsule of Example 4 | 26 | 661 | 3,387 | 218 | 158 | 172 | 427 | 420 | 149 | 152 |
| Microcapsule of Example 5 | 158 | 744 | 1,916 | 783 | 642 | 655 | 1,185 | 982 | 251 | 86 |

Industrial Applicability

In accordance with the present invention, there can be provided a sustained-release preparation with an enhanced rate of entrapment of bioactive polypeptides, inhibited early bursts of release after administration, and constant release kinetics over a long time.

What is claimed is:

1. A method of producing a sustained-release preparation which comprises, in this order:

dispersing a bioactive polypeptide in an organic solvent containing a metal salt of a biodegradeable polymer, and removing said organic solvent from the resulting dispersion to form a particulate artifact.

2. A method according to claim 1, wherein the metal salt is a polyvalent metal salt.

3. A method according to claim 1, wherein the metal salt is selected from the group consisting of a zinc salt and a calcium salt.

4. A method according to claim 1, wherein the organic solvent is a mixture of halogenated hydrocarbons and acetonitrile or alcohols.

5. A method according to claim 4, wherein the organic solvent mixture ratio of halogenated hydrocarbons to acetonitrile or alcohols is in the range of about 40:1 to about 1:1 (volume/volume).

6. A method according to claim 1, wherein the bioactive polypeptide is a hormone.

7. A method according to claim 6, wherein the hormone is an insulin.

8. A method according to claim 6, wherein the hormone is a growth hormone.

9. A method according to claim 1, wherein the bioactive polypeptide is a cytokine.

10. A method according to claim 9, wherein the cytokine is an interferon.

11. A method according to claim 1, wherein the biodegradable polymer is an aliphatic polyester.

12. A method according to claim 11, wherein the aliphatic polyester is an $\alpha$-hydroxycarboxylic acid polymer.

13. A method according to claim 11, wherein the aliphatic polyester is a lactic acid-glycolic acid copolymer.

14. A method according to claim 13, wherein the composition ratio (mol %) of lactic acid/glycolic acid of the lactic acid-glycolic acid copolymer is about 100/0 to about 40/60, and the weight-average molecular weight of the lactic acid-glycolic acid copolymer is about 3,000 to about 20,000.

15. A method according to claim 1, wherein the sustained-released preparation is a microcapsule.

16. A method according to claim 15, wherein the average particle size of the particulate artifact is about 0.1 $\mu$m to about 300 $\mu$m.

17. A method according to claim 1, wherein the sustained-release preparation is for an injection.

18. A sustained-release preparation as produced by the method according to claim 1.

19. A sustained-release preparation according to claim 18, wherein the metal content of the biodegradable polymer metal salt is about 0.01 to about 10% by weight.

20. A sustained-release preparation according to claim 18, wherein the concentration of the bioactive polypeptide is about 0.001 to about 30% (w/w).

21. A sustained-release preparation according to claim 18, wherein the bioactive polypeptide is a growth hormone.

* * * * *

UNITED STATES PATENT AND TRADEMARK OFFICE
CERTIFICATE OF CORRECTION

PATENT NO. : 6,267,981 B1
DATED : July 31, 2001
INVENTOR(S) : Kayoko Okamoto et al.

It is certified that error appears in the above-identified patent and that said Letters Patent is hereby corrected as shown below:

Title page,
Item [63], Related U.S. Application Data:
"08/714,044" should read -- 08/714,044, filed Sep. 5, 1996, now abandoned, --; and
"1996, now abandoned." should read -- 1996. --; and
Item [57], ABSTRACT:
Line 2, "broac-" should read -- bioac- --

Column 1,
Line 22, "takes" should read -- take --; and
Line 42, "extensives" should read -- extensive --.

Column 3,
Line 19, "examples" should read -- example --.

Column 6,
Line 45, "salt" should read -- salts --.

Column 10,
Line 13, "includ a" should read -- include --.

Column 12,
Line 1, "temerai-" should read -- tempera- --.

Column 13,
Line 23, "particle." should read -- particles. --;
Line 27, "microcapsul perticle" should read -- microcapsule particle --; and
Line 45, "heptitis)" should read -- hepatitis) --.

Column 16,
Line 64, "pharmaceutical" should read -- Pharmaceutical --.

UNITED STATES PATENT AND TRADEMARK OFFICE
CERTIFICATE OF CORRECTION

PATENT NO.   : 6,267,981 B1
DATED        : July 31, 2001
INVENTOR(S)  : Kayoko Okamoto et al.

It is certified that error appears in the above-identified patent and that said Letters Patent is hereby corrected as shown below:

<u>Column 22,</u>
Line 48, "released" should read -- release --.

Signed and Sealed this

Eighteenth Day of June, 2002

*Attest:*

*Attesting Officer*

JAMES E. ROGAN
*Director of the United States Patent and Trademark Office*